United States Patent
Letinois et al.

(10) Patent No.: US 10,815,178 B2
(45) Date of Patent: Oct. 27, 2020

(54) INTERMOLECULAR REACTION OF PROPARGYL ETHERS WITH DIMETHYLFURAN IN THE PRESENCE OF GOLD(I) COMPLEXES

(71) Applicant: DSM IP Assets B.V., Heerlen (NL)

(72) Inventors: Ulla Letinois, Kaiseraugst (CH); Stephan Ackermann, Kaiseraugst (CH); Jonathan Alan Medlock, Kaiseraugst (CH); Hajo Lehmann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/720,580

(22) Filed: Dec. 19, 2019

(65) Prior Publication Data

US 2020/0123087 A1    Apr. 23, 2020

Related U.S. Application Data

(62) Division of application No. 16/063,481, filed as application No. PCT/EP2016/079016 on Nov. 28, 2016, now abandoned.

(30) Foreign Application Priority Data

Dec. 21, 2015 (EP) .................................. 15201770

(51) Int. Cl.
| | |
|---|---|
| *C07C 41/30* | (2006.01) |
| *C07C 37/07* | (2006.01) |
| *C07C 37/50* | (2006.01) |
| *C07C 43/178* | (2006.01) |
| *C07D 311/72* | (2006.01) |
| *C07C 46/08* | (2006.01) |
| *C07C 41/36* | (2006.01) |
| *B01J 31/18* | (2006.01) |
| *B01J 31/22* | (2006.01) |
| *B01J 31/24* | (2006.01) |

(52) U.S. Cl.
CPC ............. *C07C 41/30* (2013.01); *B01J 31/183* (2013.01); *B01J 31/2273* (2013.01); *B01J 31/2404* (2013.01); *C07C 37/07* (2013.01); *C07C 37/50* (2013.01); *C07C 41/36* (2013.01); *C07C 43/1783* (2013.01); *C07C 46/08* (2013.01); *C07D 311/72* (2013.01); *B01J 2531/18* (2013.01)

(58) Field of Classification Search
None
See application file for complete search history.

(56) References Cited

U.S. PATENT DOCUMENTS 3,822,322 A    7/1974   Rey-Bellet et al.

FOREIGN PATENT DOCUMENTS

| EP | 0 970 953 | 1/2000 | |
|---|---|---|---|
| EP | 2842951 A1 * | 3/2015 | ........... C07D 311/70 |
| WO | 2015/110655 | 7/2015 | |

OTHER PUBLICATIONS

Shimizu et al. ("A Facile Synthesis of 4-Alkoxymethylphenols by a Copper(II)-Acetoxime Catalyst/O2 System", Tetrahedron Letters, 1991, vol. 32, No. 18, pp. 2053-2056).*
International Search Report for PCT/EP2016/079016, dated May 12, 2017, 5 pages.
Written Opinion of the ISA for PCT/EP2016/079016, dated May 12, 2017, 11 pages.
V. Sharypov et al., "Thermal conversion of alkali lignin of aspen wood in ethanol in the presence of sulfated catalysts based on zirconium dioxide", Journal of Siberian Federal University, Chemistry, Sibirskii Federal'nyi Universitet, Russia, vol. 5, No. 3, Jan. 1, 2012, pp. 251-260, English translated pp. 1-16.
N. Huguet et al., "Intermolecular Gold(I)-Catalyzed Cyclization of Furans with Alkynes: Formation of Phenols and Indenes", Chemistry—A European Journal, vol. 19, No. 21, May 17, 2013, pp. 6581-6585.
Rubio-Perez et al, "Pyridine-Enhanced Head-to-Tail Dimerization of Terminal Alkynes by a Rhodium-N-Heterocyclic-Carbene Catalyst," Chemistry A European Journal, vol. 19, Issue 45, Nov. 2013, pp. 15304-15314.

* cited by examiner

*Primary Examiner* — Rosalynd A Keys
(74) *Attorney, Agent, or Firm* — Nixon & Vanderhye P.C.

(57) ABSTRACT

The present invention relates to a method of preparing ortho substituted phenols from 2,5-dimethylfuran and propargyl ethers in the presence of a gold(I) complex. It is particularly advantageous to use 2,5-dimethylfuran as this offers an ecological beneficial synthesis of said ortho substituted phenols.

12 Claims, No Drawings

INTERMOLECULAR REACTION OF PROPARGYL ETHERS WITH DIMETHYLFURAN IN THE PRESENCE OF GOLD(I) COMPLEXES

CROSS-REFERENCE

This application is a divisional of commonly owned U.S. application Ser. No. 16/063,481, filed Jun. 18, 2018 (now abandoned), which is the U.S. national phase of International Application No. PCT/EP2016/079016, filed Nov. 28, 2016 which designated the U.S. and claims priority to EP Patent Application No. 15201770.3, filed Dec. 21, 2015, the entire contents of each of which are hereby incorporated by reference.

TECHNICAL FIELD

The present invention relates to the field of ortho-substituted phenols and their derivatives.

BACKGROUND OF THE INVENTION

Phenolic compounds are in general very interesting for a variety of industrial products and can be used particularly as intermediates for complex chemical syntheses.

Particular the class of ortho-substituted phenols, and even more of ortho-disubstituted phenols, is very appealing due their use as antioxidants.

Syntheses based on renewable raw materials are very attractive from an ecological point of view as such syntheses, as by this approach the dependency of chemical industry from the diminishing fossil oil reserves can be strongly reduced. Y. Román-Leshkov et al., Nature 2007, 447, 982-985, discloses that 2,5-dimethylfuran can be obtained from biomass. Therefore, 2,5-dimethylfuran is a very interesting building block to be used in chemical industries.

Furthermore, the use of staring materials from renewable resources are advantageous to have a better $CO_2$-balance as compared to starting materials derived from oil.

*J. Am. Chem. Soc.* 2000, 122, 11553-11554 discloses that the gold(III) salt $AuCl_3$ catalysis an intramolecular ring closure reaction of ω-alkynylfuran.

A. S. K. Hashmi et al., *Adv. Synth. Catal.* 2006, 348, 709-713 disclosed the first intermolecular reaction of a phenyl alkyne with furan using binuclear gold(I) complexes. However, in said reaction an almost equimolar amount of an alkenylfuran side product is formed next to a substituted phenol.

A. Zeiler et al., *Adv. Synth. Catal.* 2015, 357, 1507-1514 disclosed an intermolecular furan-alkynye addition. Next to phenylacetylene also different ethynyl aryl ethers are disclosed to be reacted with dimethylfuran to yield alkenylfuran or the respective phenol. In the document it is stressed that the oxygen bound directly to the triple bond plays a crucial role in said reaction.

N. Huguet et al. disclosed in *Chem. Eur. J.* 2013, 19, 6581-6585 an intermolecular gold(I) catalysed cyclization of furans with alkynes. Next to aromatic substituted alkynes such as phenylacetylene only unsubstituted short chain alkyl acetylenes have been used.

WO 2015/110655 A1 discloses the reaction of ethyne with 2,5-dimethylfuran to yield 2,5-dimethylphenol. In this reaction, however, also the corresponding 2,4-dimethylphenol is formed at considerable amounts as side products leading to a mixture of phenol isomers. WO 2015/110654 A1 discloses the reaction of reaction of propyne with 2,5-dimethylfuran to yield 2,3,6-trimethylphenol. Propyne, however, is a starting product which is difficult to handle and has a limited commercial availability.

SUMMARY OF THE INVENTION

We have found that compounds of formula (I) can be easily synthesized from 2,5-dimethylfuran in the presence of a gold(I) complex.

The starting material, i.e. 2,5-dimethylfuran can be obtained from biomass and therefore its use for the synthesis is very advantageous in view of ecological aspects.

The process is also very advantageous in that the desired product of formula (I) is formed at high selectivity and that side products (of formula (IVa) and (IVb)) can be easily separated by a further embodiment of the invention. Particularly surprising, it has been found that no phenolic side products other than the desired one are formed by said process.

The compounds of formula (I) can be used for the preparation of 2,3,6-trimethylphenol, which is an important intermediate for the synthesis of 2,3,5-trimethylbenzene-1, 4-diol (=2,3,5-trimethylhydroquinone) or of α-tocopherol, respectively and, therefore, the invention is of technically and economically high relevance.

Further aspects of the invention are subject of further independent claims. Particularly preferred embodiments are subject of dependent claims.

DETAILED DESCRIPTION OF THE INVENTION

In a first aspect, the invention relates to a process of preparing a compound of formula (I)

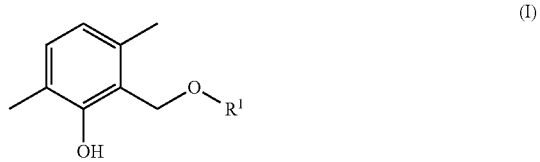

(I)

comprising the step of reacting compound of formula (II) with compound of formula (III)

(II)

(III)

wherein $R^1$ represents a $C_{1-10}$-alkyl group or a $C_{4-7}$-cycloalkyl group;
in the presence of a gold(I) complex.

The term "independently from each other" in this document means, in the context of substituents, moieties, or groups, that identically designated substituents, moieties, or groups can occur simultaneously with a different meaning in the same molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a C$_4$-alkyl group.

In case identical labels for symbols or groups are present in several formulae, in the present document, the definition of said group or symbol made in the context of one specific formula applies also to other formulae which comprises said same label.

The expression "process of preparation" is a synonym for "method of preparation" and can be used interchangeable to each other.

The anion tetra(3,5-bis(trifluoromethyl)phenyl)borate is abbreviated in the present document as "BAr$_F^-$" being known to the person skilled in the art also by the abbreviation "[BAr$^F_4$]$^-$".

Compound of formula (II) is 2,5-dimethylfuran which is commercially available.

Compound of formula (II) can be obtained from biomass such as cellulose. As biomass is a renewable raw material, the use of 2,5-dimethylfuran is very interesting from an ecological and sustainability point of view. The process of obtaining 2,5-dimethylfuran from biomass, respectively from fructose, is described in detail by Y. Roman-Leshkov et al., Nature 2007, 447, 982-985, the entire content of which is hereby incorporated by reference. Fructose is obtainable from glucose, a building block in cellulose.

The compounds of formula (III) are commercially available. These ethers can be produced for example by the reaction of propargylic alcohol with the respective dialkyl or dicycloalkyl sulfide or sulphate, particularly dimethyl sulphate, or with the respective alkyl or cycloalkyl iodide, particularly methyl iodide such as disclosed in WO 2013/056073 A1.

Preferably R$^1$ represents a C$_{1-6}$-alkyl group, particularly a C$_{1-3}$-alkyl group, more preferably a methyl group.

Said process of preparing a compound of formula (I) comprises the step of reacting compound of formula (II) with formula (III) in the presence of a gold(I) complex.

The gold(I) complex has preferably the formula [Au(I)OL]AN wherein OL represents an organic ligand and AN represents a single charged anion.

The gold(I) complex has preferably a single charged anion (AN) which is selected from the group consisting of [BX$_4$]$^-$, [PX$_6$]$^-$, [SbF$_6$]$^-$, [ClO$_4$]$^-$, CF$_3$COO$^-$, sulfonates, particularly a sulfonate of formula (AN-II), tetra(3,5-bis(trifluoromethyl)-phenyl)borate (BAr$_F^-$), tetraphenylborate, and anions of formula (AN-I)

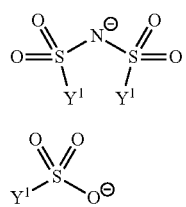

(AN-I)

(AN-II)

wherein X represents a halogen atom, particularly F or Cl; and Y$^1$ represents a phenyl or a C$_{1-8}$-alkyl group which preferably is substituted by at least one halogen atom.

Preferably Y$^1$ represents a CF$_3$ group. So, preferably, the anions of formula (AN-I) is the anion of formula (AN-Ia), i.e. the anion of bis(trifluoromethane)sulfonimide, which is also known as triflimidic acid.

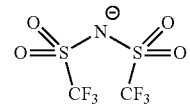

(AN-Ia)

Preferred sulfonates are halogenated anions of organic sulfonic acids, particularly of trifluoromethanesulfonic acid, which is also known as triflic acid. Therefore, the preferred sulfonates are trifluoromethanesulfonates, which are also known as triflates.

In a more preferred embodiment the anion (AN) in step b) is an anion which is selected from the group consisting of [SbF$_6$]$^-$, [BX$_4$]$^-$, triflate, and anions of formula (AN-I).

A particularly preferred anion is [SbF$_6$]$^-$.

It is preferred that the gold(I) complex has an organic ligand (OL) which is either at least one phosphorous containing ligand, particularly a phosphorous containing ligand which is selected from the group consisting of formula (P1), (P2), (P3), (P4), (P5), (P6), (P7) and (P8);

or at least an imidazole-2-ylidene ligand, particularly 1,3-bis(2,6-diisopropylphenyl)-1,3-dihydro-2H-imidazol-2-ylidene (=compound of formula (IM));

or at least an 1H-1,2,3-triazol ligand, particularly of formula (TR-1) or (TR-2) or (TR-3), more particularly of formula (TR-3);

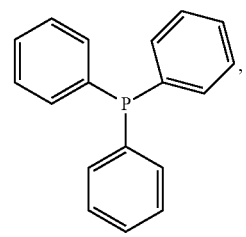

(P1)

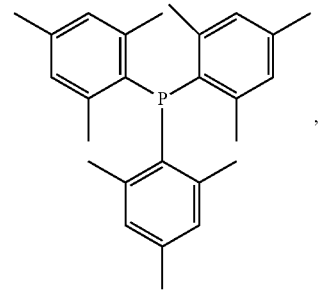

(P2)

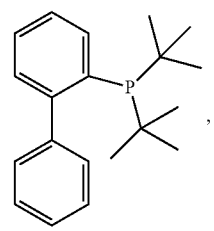

(P3)

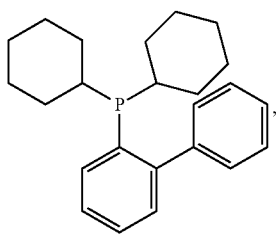
(P4)

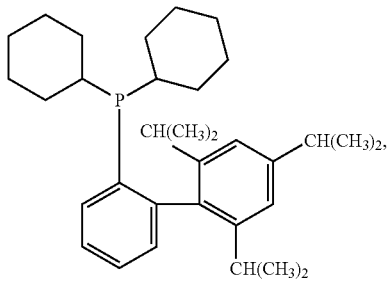
(P5)

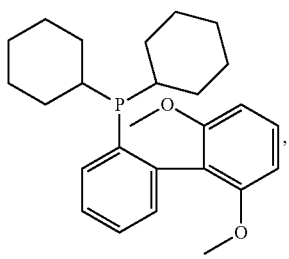
(P6)

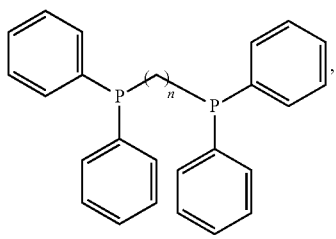
(P7)

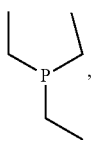
(P8)

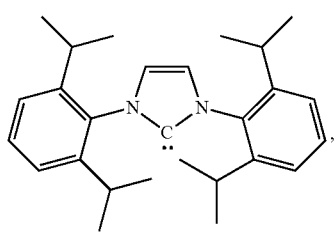
(IM)

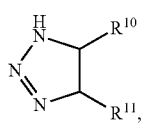
(TR-1)

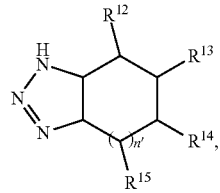
(TR-2)

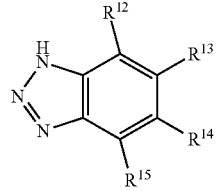
(TR-3)

wherein $R^{10}$ and $R^{11}$ represent independently from each other either H or a linear or branched $C_{1-10}$-alkyl or $C_{4-10}$-cycloalkyl group;

and wherein $R^{12}$, $R^{13}$, $R^{14}$ and $R^{15}$ represent independently from each other H or a linear or branched $C_{1-6}$-alkyl group;

n stands for an integer of 1-6 and n' stands for 0 or 1 or 2.

The organic ligand (OL) of formula (P4) is also known as CyJohnPhos.

The synthesis of these organic ligands (OL) is known to the person skilled in the art.

The Au(I) complex can be added to one or a mixture of the starting material of compound of formula (II) and/or formula (III) as such, i.e. particularly in the form of a gold(I) complex of formula [Au(I)OL]AN, or the Au(I)-complex is formed in situ in one of the starting material or the reaction mixture (before or after the reaction has started).

The gold(I) complex is preferably formed in situ in the reaction mixture.

Particularly, the gold(I) complex is prepared from a gold(I) chloro complex and a silver(I) salt. The silver(I) salt is preferably Ag(I)AN. The organic ligand is in this case either present in the reaction of the gold(I) chloro complex with the silver(I) salt or is part of the gold(I) complex. By this reaction the desired gold(I) complex, i.e. preferably [Au(I)OL]AN, is prepared. AgCl formed by this reaction as precipitate does not interfere negatively with the reaction of preparing the compound of formula (I).

Hence, the gold (I) complex is preferably of formula [Au(I)OL]AN wherein OL represents an organic ligand and AN represents a single charged anion and the gold (I) complex is prepared by the reaction of Au(I)OLCl and AgAN.

Preferred Au(I) complexes of the formula [Au(I)OL]AN are selected from the group consisting of

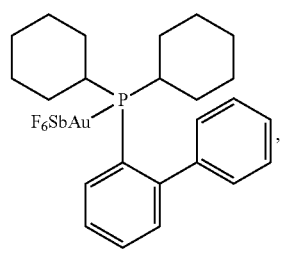

-continued

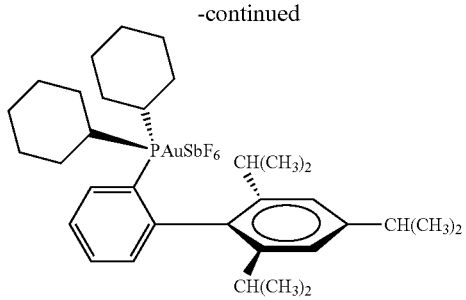

and [Au(I)P6]AN-Ia, wherein P6 is the organic ligand of formula (P6) and AN-Ia is the anion of formula (AN-Ia).

In another preferred embodiment, the gold (I) complex is of formula [Au(I)OL]AN wherein OL represents an organic ligand and AN represents a single charged anion and the gold (I) complex is prepared by the reaction of Au(I)OLCl and NaAN. This reaction is particularly preferred if AN is $[BAr^F_4]^-$.

The gold(I) complex is used typically in a molar ratio of gold(I) complex to compound of formula (II) of 1:2 to 1:10'000, particularly 1:10 to 1:3'000, preferably 1:25 to 1:3'000.

The molar ratio of compound of formula (II) to compound of formula (III) is preferably between 0.05 and 10, more preferably between 0.1 and 2, even more preferably between 0.2 and 1.5.

In another embodiment the molar ratio of compound of formula (II) to compound of formula (III) is <1, preferably <0.8, more preferably <0.5.

The most preferred compound of formula (I) is 2-(methoxymethyl)-3,6-dimethylphenol:

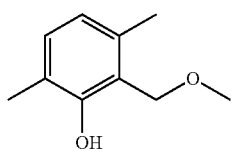

The reaction is preferably carried out under normal pressure (i.e. 1013 mbar). The reaction temperature is particularly between 0-50° C., preferably between 15-30° C.

The reaction is usually carried out in an inert solvent (or mixture of inert solvents). Preferably the solvent (or the mixture of solvents) has a pH of 7 or less than 7. Preferred solvents are halogenated solvents, particularly dichloromethane, 1,2-dichloroethane, chloroform or 2,2,2-trifluoroethanol; or toluene, ethyl acetate, cyclohexanone or acetone. More preferred, the solvents are dichloromethane and 1,2-dichloroethane.

It has been observed that particularly mixtures of dichloromethane and 2,2,2-trifluoroethanol, preferably in an excess of dichloromethane, more preferably a mixture of dichloromethane with 5% by volume of 2,2,2-trifluoroethanol, are very suitable for obtaining a high selectivity of compound of formula (I).

It has been observed that the reaction as described above forms also compounds of formula (IVa) and/or formula (IVb) as products of side reactions. However, it has been surprisingly found that the formation of compound of formula (I) is much preferred over the formation of these side products. Therefore, the compound of formula (I) is formed at unexpected high selectivity and high yield.

Said products can be identified/quantified by GC/MS and NMR.

Compounds of formula (IVa) and/or formula (IVb) are, therefore, formed only in minor amounts.

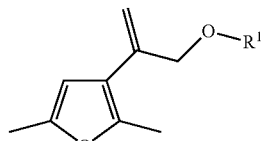
(IVa)

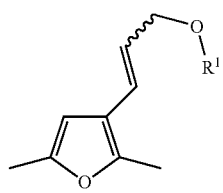
(IVb)

Particular the total amount of compound of formula (IVa) and (IVb) is at most 80% by weight, preferably at most 70% by weight, more preferably at most 50% by weight, even more preferably at most 20% by weight, most preferably at most 10% by weight, relative to the weight of compound of formula (I).

Particularly important is to note that no formation of molecules of formula (I') have been observed in the above reaction.

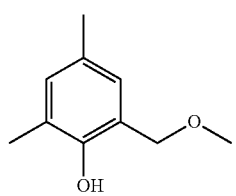
(I')

This is very surprising as in case of the corresponding reaction of ethyne with 2,5-dimethylfuran as disclosed in WO 2015/110655 A1 next to the desired 2,5-dimethylphenol considerable amounts (I-a) also considerable amounts of 2,4-dimethylphenol (I-b) are formed.

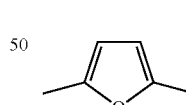 + ≡ ⟶ 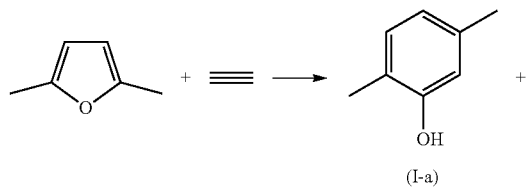
(I-a)

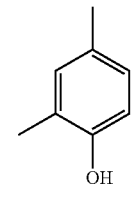
(I-b)

These phenolic isomers (I-a)/(I-b) are very difficult to be separated from each other due to their similar structures.

Therefore, in contrast to these reactions of the state of the art, only one phenolic reaction product, i. e. compound of formula (I), is formed in the process of the present invention.

It has been observed that the products of the side reaction, i.e. compounds of formula (IVa) and/or formula (IVb), can be easily separated from compound of formula (I) due to their strongly different structure as compared to compound of formula (I).

In a preferred embodiment the process of preparing a compound of formula (I) comprising the step of reacting compound of formula (II) with compound of formula (III) as disclosed above comprises a subsequent step a):

a) separating the compound of formula (I) from compound of formula (IVa) and/or formula (IVb)

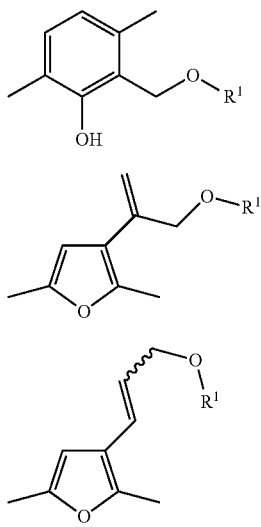

wherein the wavy line represents a carbon-carbon bond which is linked to the adjacent carbon-carbon double bond so as to have said carbon-carbon double bond either in the Z or in the E-configuration.

The separation can be achieved by different separation methods such as distillation or chromatography.

Preferably compound of formula (I) is separated from compound of formula (IVa) and/or (IVb) by chromatography, particularly by using silica gel as stationary phase.

Chromatographic separation is known per se as standard purification method. Particularly flash chromatography is suitable. For industrial purposes particularly Simulated Moving Bed (SMB) chromatography is very suitable for this separation.

By such an additional chromatographic separation, it can be achieved to obtain the desired compound of formula (I) in pure form, i.e. it is possible by optimizing said separation that the compounds of formula (IVa) and/or formula (IVb) are reduced in amount below the threshold of analytical detection.

Hence, in a further aspect the invention relates to compound of formula (I).

In an even further aspect the invention relates to a composition comprising the compound of formula (I) and at least the compound of formula (IVa) or (IVb)

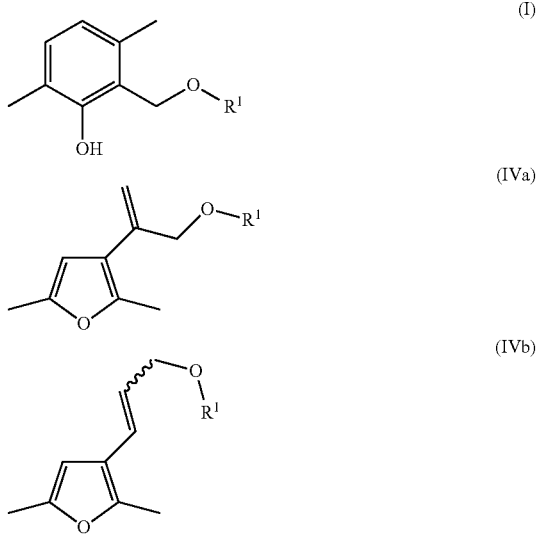

wherein $R^1$ represents a $C_{1-10}$-alkyl group or a $C_{4-7}$-cycloalkyl group and the wavy line represents a carbon-carbon bond which is linked to the adjacent carbon-carbon double bond so as to have said carbon-carbon double bond either in the Z or in the E-configuration.

As mentioned above already for compound of formula (I), it is preferred that that $R^1$ represents a $C_{1-6}$-alkyl group, preferably a $C_{1-3}$-alkyl group, more preferably a methyl group.

It is further preferred that in said composition the total amount of compound of formula (IVa) and (IVb) is at most 80% by weight, preferably at most 70% by weight, more preferably at most 50% by weight, even more preferably at most 20% by weight, most preferably at most 10% by weight, relative to the weight of compound of formula (I).

By using separation method as mentioned above the total amount of compound of formula (IVa) and (IVb) can be easily further reduced. Therefore, it is easily achievable that the total amount of compound of formula (IVa) and (IVb) after additional separation step, such as chromatography, is at most 1% by weight, preferably at most 0.5% by weight, more preferably at most 0.1% by weight, relative to the weight of compound of formula (I). In a preferred embodiment pure compound of formula (I) is obtained after the separation step.

Compounds of formula (I), particularly been prepared according to the process as disclosed above in great detail, are particularly useful as intermediate for the synthesis of 2,3,6-trimethylphenol, which is an important intermediate for the synthesis of 2,3,5-trimethylbenzene-1,4-diol (=2,3,5-trimethylhydroquinone) or of α-tocopherol, respectively. Therefore, another aspect of the present invention relates to a process of reducing a compound of formula (I)

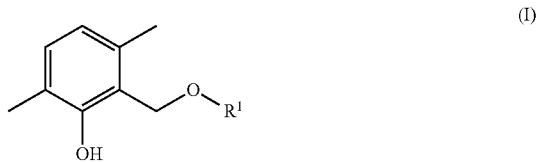

by a reducing agent in the presence of a heterogeneous metal catalyst to yield a compound of formula (A)

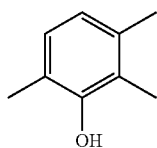

(A)

wherein the metal is selected from the group consisting of Ni, Fe, Ir, Pd, Pt, Rh and Ru;

wherein $R^1$ represents a $C_{1-10}$-alkyl group or a $C_{4-7}$-cycloalkyl group.

Compound of formula (I) is reduced in the above process by a reducing agent.

In one preferred embodiment the reducing agent is molecular hydrogen. In other words, in one embodiment the compound of formula (I) is hydrogenated by molecular hydrogen in the presence of a heterogeneous metal catalyst.

In another preferred embodiment the reducing agent is a transfer hydrogenation agent. In other words, in another embodiment the compound of formula (I), is transfer hydrogenated by a transfer hydrogenation agent. Said transfer hydrogenation agent is preferably formic acid and/or a formic acid salt.

The compound of formula (I) is reduced by a reducing agent in the presence of a heterogeneous metal catalyst wherein the metal is selected from the group consisting of Ni, Fe, Ir, Pd, Pt, Rh and Ru.

It is preferred that the metal of the heterogeneous metal catalyst comprises at least one of the metals selected from the group consisting of Ni, Fe, Ir, Pd, Pt and Rh. The heterogeneous metal catalyst can be a catalyst comprising more than one of the mentioned metals.

Particularly, the heterogeneous metal catalyst comprises Pd and Pt as metal.

It is preferred that the metal of the heterogeneous metal catalyst is palladium.

A wide variety of heterogeneous metal catalysts are known. Particularly useful are heterogeneous metal catalyst which are on a carrier or support material. Such carrier material is particularly a solid material having a high surface area, to which the metal is affixed. The support may be inert or participate in the catalytic reactions. Typical supports/carrier material include various kinds of carbon, alumina, and silica. The preferred support/carrier material is carbon.

The heterogeneous metal catalyst may also be affixed or immobilized on a surface of a larger object typically in form of a structured packing element which might be a part of the reactor in which the reduction takes place or an element which is inserted into said reactor. This structured packing element may be a dumped packing, a knit, an open-celled foam structure, preferably made of plastic, for example polyurethane or melamine resin, or ceramic, or a structured packing element, as already known in principle, i.e. by its geometric shape, from distillation and extraction technology. However, for the purposes of the present invention, structured packings in principle have a substantially smaller hydraulic diameter, frequently by a factor of from 2 to 10, than comparable internals in the field of distillation and extraction technology. Useful structured packing elements are in particular metal fabric packings and wire fabric packings, for example of the design Montz A3, Sulzer BX, DX and EX. Instead of metal fabric packings, it is also possible to use structured packings made of other woven, knitted or felted materials. Further useful structured packings are of flat or corrugated sheets, preferably without perforation, or other relatively large orifices, for example corresponding to the designs Montz BI or Sulzer Mellapak. The structured packings made of expanded metal are also advantageous, for example structured packings of the type Montz BSH.

It is preferred that the heterogeneous metal catalyst is a palladium catalyst, particularly a palladium on carbon catalyst (Pd/C).

The catalytic metal loading (i.e. weight metal/weight (metal+carrier)) is typically between 1 to 20%, preferably between 4 and 11%, more preferably between 4 and 6%, by weight. A very preferred heterogeneous metal catalyst is palladium on carbon catalyst (Pd/C) of which 5% by weight is palladium (i.e. loading=5%).

The reduction can be carried out in the presence or absence of solvents. Suitable solvents are particularly those in which the compound of formula (I) is soluble. Particularly, the solvent is an organic solvent, preferably a solvent selected from the group consisting of alcohols, preferably the alcohol of formula $R^1OH$, or ethers, preferably dialkyl ether or cyclic ethers, preferably tetrahydrofuran. $R^1OH$ is the alcohol which is formed in the reduction reaction as mentioned above.

Furthermore, suitable additives may be added to the reaction mixture of the compound of formula (I), the heterogeneous metal catalyst and the reducing agent. Particularly, organic acids, preferably acetic acid, can be added to the mixture before or during the reduction.

The reduction is performed typically at temperatures of between 20 and 80°, particularly between 30 and 50° C., and preferably under a pressure. In case of use of molecular hydrogen, it is preferred that the reduction is carried out under a pressure of hydrogen of between 2 and 20 bar, preferably of between 3 and 7 bar.

The reduction is performed in a suitable vessel. The reduction can be made batchwise or continuously. Suitable reactors for industrial scale are known.

It is preferred that the weight ratio of the heterogeneous metal catalyst to the compound of formula (I) is 0.01% to 20%, particularly 1% to 10%.

It has been observed that the process as described above yields efficiently a compound of formula (A)

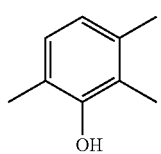

(A)

It has been also observed that the above process is surprisingly suited for the reduction of compound (I) as it has been observed that reduction of molecules having a very similar chemical structure as compared with compound of formula (I) could not be reduced to the corresponding (poly)alkylphenols.

As mentioned above, 2,3,6-trimethylphenol, i.e. compound of formula (A), is an important intermediate for the synthesis of 2,3,5-trimethylbenzene-1,4-diol (=2,3,5-trimethylhydroquinone) or of α-tocopherol, respectively.

Hence, a further aspect of the present invention is a process for the manufacture of the compound of formula (C) from compound of formula (I) comprising the following steps a') reducing the compound of formula (I) by the process as disclosed above in great detail to yield a compound of formula (A);

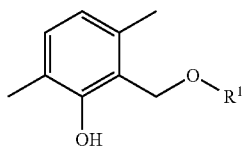

(I)

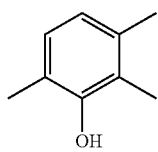

(A)

b') oxidizing the compound of formula (A) to yield a compound of formula (B) by an oxidizing agent

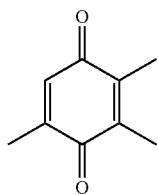

(B)

c') reducing the compound of formula (B) to yield a compound of formula (C) by a reducing agent

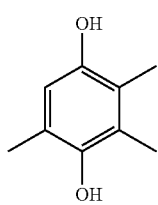

(C)

In step b') the compound of formula (A) is oxidized to the compound of formula (B). The oxidation is preferably carried out by any suitable method known in the art, for example: with air using salcomine as catalyst in ethanol according to the procedure published by A. Stocker, W.-D. Woggon, A. Rüttimann, *Helv. Chim. Acta* 1993, 76, 1729-1738, or by copper and molecular oxygen as described in EP 0127888 A1 or by the use of a heteropoly acid and oxygen as described by Kholdeeva et al in *Journal of Molecular Catalysis,* 75 (1992) 235-244, the entire content of which is hereby incorporated by reference.

In step c') the compound of formula (B) is reduced to compound of formula (C). The reduction can be performed by hydrogenation or be achieved with sodium dithionite in water according to the method as disclosed by K. Sato, Y. Fujima, A. Yamada *Bull. Chem. Soc. Jap.* 1968, 41, 442-444, the entire content of which is hereby incorporated by reference.

Compounds of formula (C) can be used directly in various fields or can be used as important starting materials for the synthesis of compounds suitable for the synthesis of compounds useful in pharmaceuticals, food or feed supplements, cosmetics, or flavors and fragrances.

Particularly important is the use of compound of formula (C) as antioxidant, in plastics, adhesives, inks, composites, or in organisms.

The compound of formula (A) is particularly important as it can be used as a starting material for the synthesis of α-tocopherol.

Therefore, in a further aspect, the invention relates to a process for the manufacture of compound of formula (D) from compound of formula (I) comprising the steps a') hydrogenate compound of formula (I) by the process as disclosed above in great detail to yield a compound of formula (A);

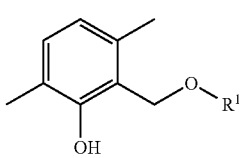

(I)

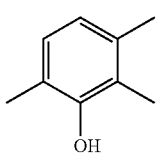

(A)

b') oxidizing the compound of formula (A) to yield a compound of formula (B) by an oxidizing agent

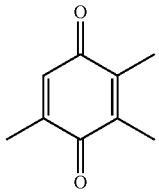

(B)

c') reducing the compound of formula (B) to yield a compound of formula (C) by a reducing agent

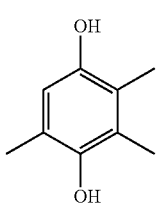

(C)

d') condensing isophytol with the compound of formula (C) to yield a compound of formula (D);

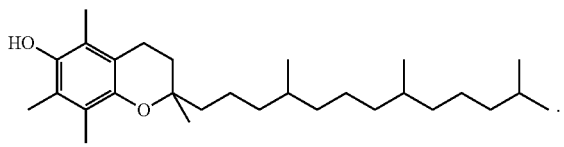
(D)

In step d') isophytol (=3,7,11,15-tetramethylhexadec-1-en-3-ol) is condensed with a compound of formula (C) to yield a compound of formula (D). Isophytol and a compound of formula (C), described as step d), is known by the person skilled in the art. For this condensation a series of catalysts may be used such as $ZnCl_2$/mineral acid, $BF_3/AlCl_3$, Fe/HCl, trifluoroacetic acid or boric acid/carboxylic acid as well as indium(III) or scandium(III) salts as disclosed in WO 2005/121115 A1. Furthermore, suitable catalysts are heteropoly acids, particularly 12-tungstophosphoric acid or 12-tungstosilicic acid such as disclosed in EP 0 970 953 A1, the entire content of which is hereby incorporated by reference.

EXAMPLES

The present invention is further illustrated by the following experiments.

Formation of Gold (I) Complex

In a glovebox 380.2 mg chloro[1,3-bis(2,6-diisopropylphenyl)imidazol-2-ylidene]gold(I) (=0.61 mmol) and 210.4 mg silverhexafluoroantimonate (=0.61 mmol) or 543 mg sodium tetra(3,5-bis(trifluoromethyl)phenyl)borate (=0.61 mmol) and 61.3 μl benzonitrile are weighed in a 25 ml round bottom flask which is equipped with a magnetic stirring bar and argon supply. During this procedure the gold (I) complex $[Au(I)IM]SbF_6$ respectively $[Au(I)IM]BAr_F$, IM being the organic ligand of formula (IM) has been formed.

Formation of 2-(methoxymethyl)-3,6-dimethylphenol

To the above mentioned mixture 10 ml of dichloromethane or a mixture of dichloro-methane/2,2,2-trifluoroethanol (95/5 vol %) are admixed outside the glovebox and 5.364 ml 2,5-dimethylfuran (=50 mmol), respectively 1.072 ml (=10 mmol) (="DMF") are added and cooled to 0° C., followed by addition of 0.87 ml methylpropargylether (=10 mmol) (="MPE") The reaction mixture has turned blue and darkens on further agitation. The reaction mixture is agitated at 23° C. under argon for a further 120 hours.

After concentrating under reduced pressure at 40° C. and 20 mbar the residue formed has been taken up in 60 ml of dichloromethane.

The dried residue has been analyzed by gas chromatography. The amounts of 2-(methoxymethyl)-3,6-dimethylphenol (="(I)") and the total amounts of the respective alkenylfuran compounds of formula (IVa) or (IVb) ($R^1$=$CH_3$) ("(IVa)/(IVb)") have been indicated in table 1 in GC-area-%.

TABLE 1

| Ex. | Catalyst | DMF/MPE [w/w] | Solvent | [(I)] [%] | [(IVa)/(IVb)] [%] | $\frac{[(IVa)/(IVb)]}{[(I)]}$ [%] |
|---|---|---|---|---|---|---|
| 1 | $[Au(I)IM]SbF_6$ | 5:1 | DCM/TFE[1] | 42 | 1 | 2.4 |
| 2 | $[Au(I)IM]BAr_F$ | 5:1 | DCM/TFE[1] | 42 | 30 | 71 |
| 3 | $[Au(I)IM]SbF_6$ | 5:1 | DCM[2] | 48 | 31 | 65 |
| 4 | $[Au(I)IM]SbF_6$ | 5:1 | TFE[3] | 33 | 15 | 45 |
| 5 | $[Au(I)IM]SbF_6$ | 5:1 | DCM[2] | 32 | 24 | 75 |
| 6 | $[Au(I)IM]BAr_F$ | 0.8:1 | DCM[2] | 51 | 8 | 16 |

Formation of 2-(methoxymethyl)-3,6-dimethylphenol
[1]DCM/TFE = dichloromethane/2,2,2-trifluorethanol (95/5 w/w)
[2]DCM = dichloromethane
[3]TFE = 2,2,2-trifluorethanol (95/5 w/w)

The residue has been in a further step purified by chromatography over 40 g silica gel column (particle size: 40-63 μm) with cyclohexane/ethylacetate (95:5 vol/vol) as eluent to yield pure 2-(methoxymethyl)-3,6-dimethylphenol. 2-(methoxymethyl)-3,6-dimethylphenol has been identified by $^1$H-NMR, $^{13}$C NMR and GC/MS.

For GC/MS analysis, the sample was treated with N,O-bis(trimethyl-silyl)trifluoroacetamide (BSTFA) and pyridine. When in the GC/MS analysis a $Si(CH_3)_3$ fragment of a particular species was observed, this was an indication for the presence of a free hydroxylgroup, such as in phenol. In the hydroarylated products (formula (IVa) or (IVb)), the presence of trimethylsilyl fragments was not observed.

2-(methoxymethyl)-3,6-dimethyl Phenol

GC/MS ($M^+$=166 g/mol). Silylation observed $^1$H NMR (300 MHz, $CDCl_3$, δ in ppm): δ=2.20 (s, 3H); 2.21 (s, 3H); 3.45 (s, 3H); 4.71 (s, 2H); 6.59 (d, J=7.56 Hz, 1H); 6.94 (d, J=7.56 Hz, 2H); 8.01 (s, 1H).

$^{13}$C-NMR (75 MHz, $CDCl_3$, δ in ppm): δ=15.6; 19.1; 58.3; 70.8; 119.4; 121.3; 123.2; 129.9; 133.4; 154.8.

Hydroarylated Compound of Formula (IVa) or (IVb)

GC-MS: $M^+$=166.1 g/mol. No silylation observed.

$^1$H NMR (300 MHz, $CDCl_3$, δ in ppm): δ=2.20 (s, 3H); 2.33 (s, 3H); 3.35 (s, 3H); 4.09 (d, J=0.75 Hz, 2H); 5.14 (d, J=1.59; 1H); 5.5.22 (d, J=1.59 Hz, 1H); 6.00 (s, 1H).

$^{13}$C-NMR (75 MHz, $CDCl_3$, δ in ppm): δ=13.2; 13.3; 57.8; 75.3; 105.9; 113.2; 119.3; 137.9; 146.8; 149.4.

Formation of 2,3,6-trimethylphenol (Example 7)

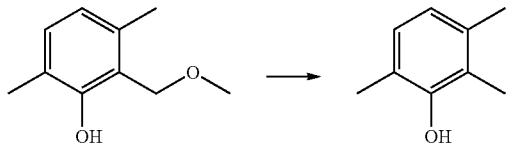

2-(methoxymethyl)-3,6-dimethylphenol (32 mg) (as prepared above) was dissolved in methanol (1.0 g) and 5% palladium on carbon (Evonik E 101 N/D, 3 mg) was added. The reactor was sealed and purged three times with nitrogen and three times with hydrogen. The mixture was stirred at 40° C. under 5 bar hydrogen pressure for 22 hours. An additional 3 mg of 5% palladium on carbon was added and the mixture was stirred at 40° C. under 5 bar hydrogen pressure for a further 22 hours. The pressure was released, the catalyst was removed by filtration and the mixture evaporated under reduced pressure to give a crude product. GC-MS analysis showed full conversion and 98.5% purity product (yield 98%).

Comparative Examples 5-methyl-1,3-dihydroisobenzofuran-4-ol or 3-(methoxymethyl)phenol, respectively, have been submitted to the same reduction conditions as for example 7 with the object to yield 2,3,6-trimethylphenol, or m-cresol, respectively. However, in both cases, the desired product has not been detected.

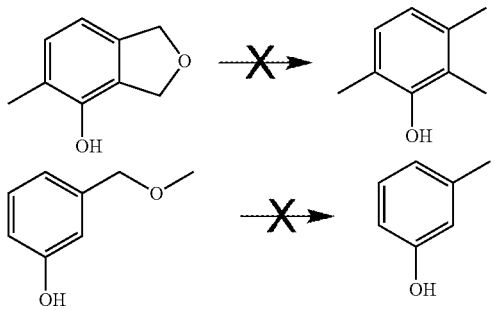

The invention claimed is:

1. A process which comprises:
(i) producing a compound of formula (I):

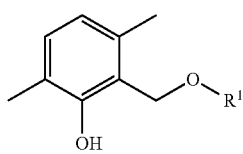

(I)

wherein $R^1$ represents a $C_{1-10}$-alkyl group or a $C_{4-7}$-cycloalkyl group by reacting in the presence of a gold(I) complex a compound of formula (II):

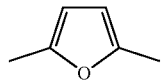

(II)

with compound of formula (III):

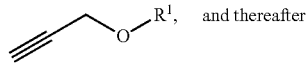

(III)

(ii) reducing the compound of formula (I) by a reducing agent in the presence of a heterogeneous metal catalyst to yield a compound of formula (A):

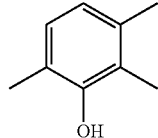

(A)

wherein the metal is selected from the group consisting of Ni, Fe, Ir, Pd, Pt, Rh and Ru.

2. The process according to claim 1, wherein $R^1$ represents a $C_{1-6}$-alkyl group.

3. The process according to claim 1, wherein the gold(I) complex has the formula:

[Au(I)OL]AN wherein OL represents an organic ligand and AN represents a single charged anion.

4. The process according to claim 1, wherein the gold(I) complex has a single charged anion (AN) which is selected from the group consisting of $[BX_4]^-$, $[PX_6]^-$, $[SbF_6]^-$, $[ClO_4]^-$, $-CF_3COO^-$, a sulfonate of formula (AN-II), tetra (3,5-bis(trifluoromethyl)phenyl)borate $(BAr_F^-)$, tetraphenylborate, and anions of formula (AN-I):

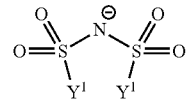

(AN-I)

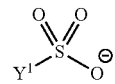

(AN-II)

wherein
X represents a halogen atom; and
$Y^1$ represents a phenyl or a $C_{1-8}$-alkyl group which optionally is substituted by at least one halogen atom.

5. The process according to claim 1, wherein the gold(I) complex has an organic ligand (OL) which is either
(i) at least one phosphorous containing ligand which is selected from the group consisting of formula (P1), (P2), (P3), (P4), (P5), (P6), (P7) and (P8);
(ii) at least an imidazole-2-ylidene ligand compound of formula (IM): or
(iii) at least a 1H-1,2,3-triazol ligand of formula (TR-1), or (TR-2) or (TR-3):

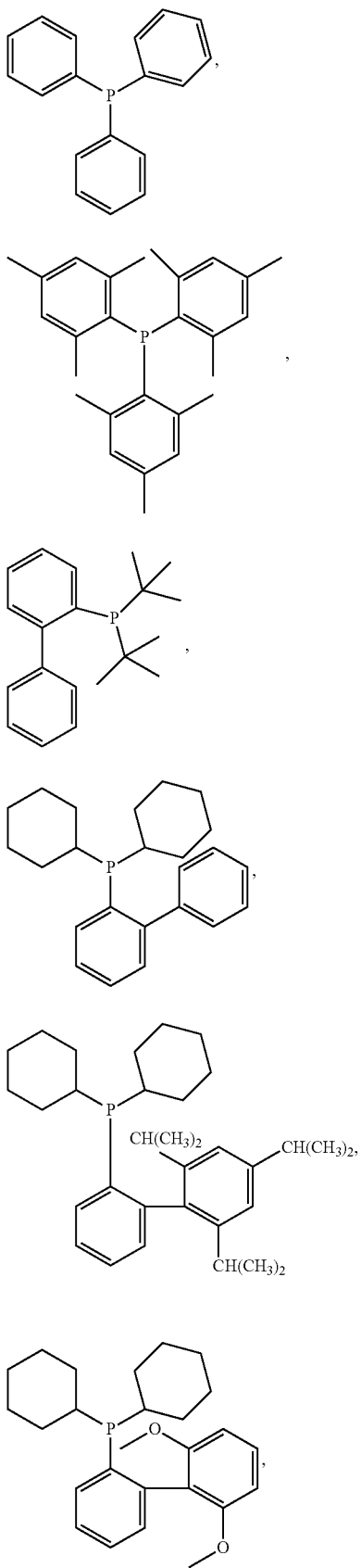

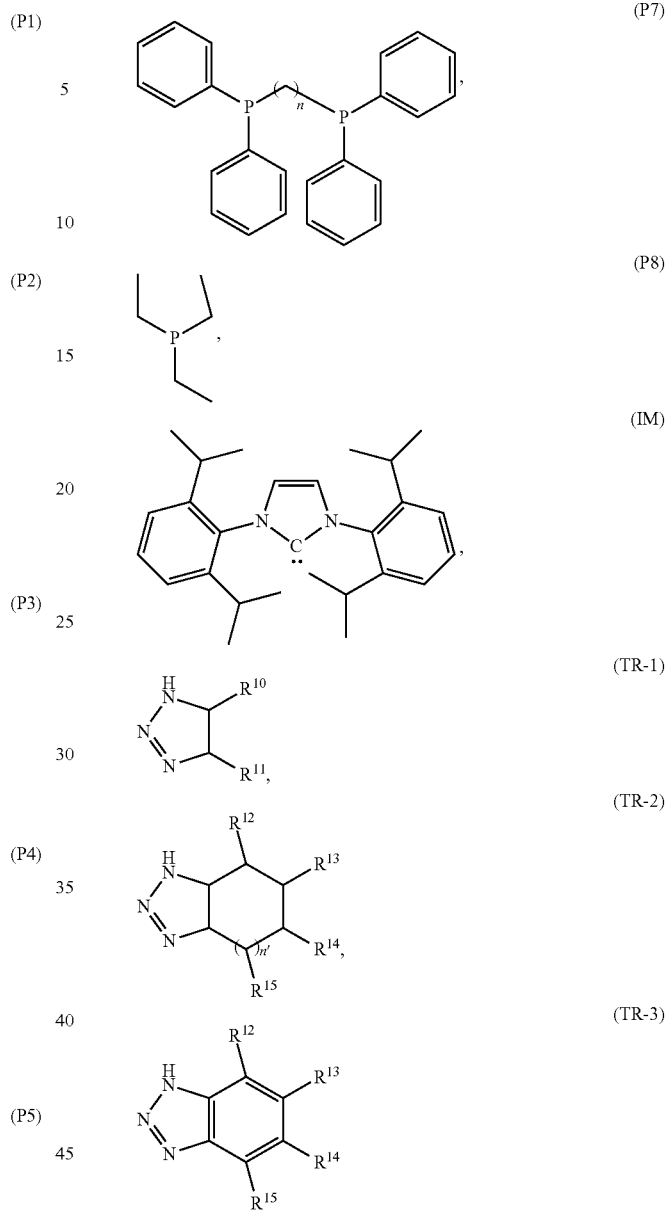

wherein
R¹⁰ and R¹¹ represent independently from each other either H or a linear or branched $C_{1-10}$-alkyl or $C_{4-10}$-cycloalkyl group; and wherein
R¹², R¹³, R¹⁴ and R¹⁵ represent independently from each other H or a linear or branched $C_{1-6}$-alkyl group;
n stands for an integer of 1-6, and
n' stands for 0, 1 or 2.

6. The process according to a claim 1, wherein the gold(I) complex is prepared from a gold(I) chloro complex and a silver(I) salt.

7. The process according to claim 6 wherein 1 the gold (I) complex is of formula:

[Au(I)OL]AN wherein OL represents an organic ligand and AN represents a single charged anion, and
wherein the gold (I) complex is a reaction product of Au(I)OLCl and AgAN.

8. The process according to claim 1, wherein the gold (I) complex is of formula:

[Au(I)OL]AN wherein OL represents an organic ligand and AN represents a single charged anion, and wherein the gold (I) complex is a reaction product of Au(I)OLCl and NaAN.

9. The process according to claim 1, wherein step (i) comprises:

ia) separating the compound of formula (I) from a compound of formula (IVa) and/or formula (IVb):

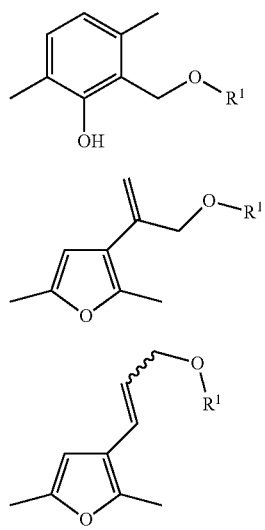

(I)

(IVa)

(IVb)

wherein the wavy line represents a carbon-carbon bond which is linked to the adjacent carbon-carbon double bond so as to have the said carbon-carbon double bond either in a the Z or in an the E-configuration.

10. The process according to claim 9, wherein step (ia) comprises separating the compound of formula (I) from the compound of formula (IVa) and/or (IVb) are by chromatography.

11. A process for the manufacture of a compound of formula (C) from a compound of formula (I), wherein the process comprises the following steps of:

a') reducing the compound of formula (I) by the process according to claim 1 to yield a compound of formula (A):

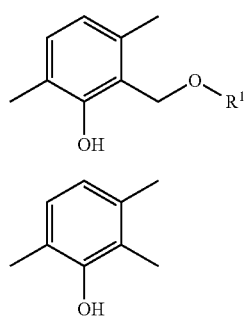

(I)

(A)

b') oxidizing the compound of formula (A) by an oxidizing agent to yield a compound of formula (B):

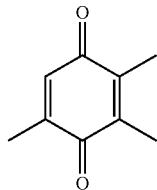

(B)

c') and thereafter reducing the compound of formula (B) by a reducing agent to yield a compound of formula (C):

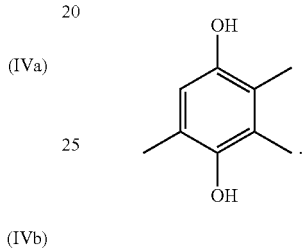

(C)

12. A process for the manufacture of a compound of formula (D) from a compound of formula (I) comprising the steps:

a') hydrogenating a compound of formula (I) by the process according to claim 1 to yield compound of formula (A):

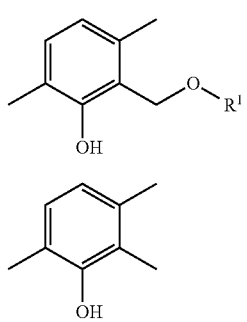

(I)

(A)

b') oxidizing the compound of formula (A) by an oxidizing agent to yield a compound of formula (B):

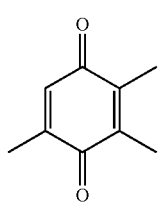

(B)

c') reducing the compound of formula (B) by a reducing agent to yield a compound of formula (C):

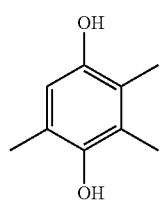 (C)
d') and thereafter condensing isophytol with the compound of formula (C) to yield a compound of formula (D):
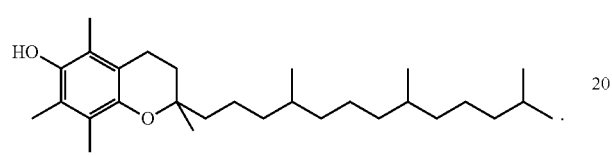 (D)
* * * * *